United States Patent [19]
Lee et al.

[11] 3,971,818
[45] July 27, 1976

[54] METHOD OF PREPARING OLEFINIC SILOXANE BY GLC

[75] Inventors: Chi-Long Lee; Ollie W. Marko, both of Midland, Mich.

[73] Assignee: Dow Corning Corporation, Midland, Mich.

[22] Filed: Dec. 2, 1974

[21] Appl. No.: 528,959

[52] U.S. Cl. .................. 260/448.2 E; 260/448.8 R
[51] Int. Cl.$^2$...................... C07F 7/08; C07F 7/18
[58] Field of Search ............................ 260/448.2 E

[56] References Cited
UNITED STATES PATENTS

| | | | |
|---|---|---|---|
| 2,823,218 | 2/1958 | Speier et al. | 260/448.2 E |
| 2,970,150 | 1/1961 | Bailey | 260/448.2 E X |
| 3,419,593 | 12/1968 | Willing | 260/448.2 E |
| 3,453,233 | 7/1969 | Flatt | 260/448.2 E X |
| 3,516,946 | 6/1970 | Modic | 260/448.2 E X |
| 3,576,027 | 4/1971 | Fish | 260/448.2 E |
| 3,793,358 | 2/1974 | Bauer et al. | 260/448.2 E |

*Primary Examiner*—Paul F. Shaver
*Attorney, Agent, or Firm*—Roger H. Borrousch

[57] ABSTRACT

Injecting a mixture of an acetylenic alcohol and a siloxane compound having at least three silicon-bonded hydrogen atoms into a gas liquid chromatographic (GLC) column through an injection port heated at 300°C. to 375°C. and coated with a layer of a platinum catalyst where the column is heated at 100°C. to 375°C. provides an olefinic siloxane compound which is, below 100°C., an inhibitor for the reaction between the acetylenic alcohol and the siloxane compound having at least three silicon-bonded hydrogen atoms in the presence of a platinum catalyst. This method provides high purity products which do not need further distillation and which do not contain platinum.

9 Claims, No Drawings

METHOD OF PREPARING OLEFINIC SILOXANE BY GLC

BACKGROUND OF THE INVENTION

1. Field of the Invention

This invention relates to a method of preparing a siloxane compound having olefinic unsaturation by using a GLC column.

2. Description of the Prior Art

The reaction between compounds having aliphatically unsaturated carbon linkages such as C=C or C≡C with silicon compounds having silicon-bonded hydrogen atoms in the presence of platinum to form new silicon compounds is well known in the art and is known as hydrosilation. A patent by John L. Speier and Donald E. Hook, U.S. Pat. No. 2,823,218, teaches that such reactions can be carried out in the presence of chloroplatinic acid. Speier et al. teach that both olefinic compounds and acetylenic compounds readily react to form new silicon compounds wherein the SiH adds across the unsaturated carbon bonds with a high product yield. Speier et al. also teach that the presence of other substituents in the unsaturated molecule, whether they be functional or entirely inert, does not prohibit the reaction. The unsaturated compounds which undergo reaction are taught as including unsaturated alcohols such as allyl alcohol, methylvinylcarbinol and ethynyldimethylcarbinol. Speier et al. teach that if an unsaturated alcohol is employed, a competing alcoholysis reaction will take place, but the reactants will no longer be those introduced where the source for the SiH is a silane, however, in general this problem does not arise when a siloxane is used as the source of SiH because the siloxanes are relatively inert to any extraneous substituents in the unsaturated reactant.

Speier et al. teach that the reaction temperature can vary over an extremely wide temperature range and optimum temperatures depend upon the concentration of catalyst present and the nature of the reactants. Temperatures suggested range from 0°C. to below 300°C. The temperature should be such that at least one of the reactants or a portion of the reaction mixture is in a mobile stage, liquid or gaseous and the maximum temperature is determined only by the stability of the reactants and the operator's desire to avoid decomposition products.

Speier et al. teach that the reaction time is variable and depends upon the reactants, reaction temperature and catalyst concentration among other things. Contact times of greater than 16 or 17 hours do no harm unless an extremely elevated temperature is employed, however, many reactants give a practically quantitative yield with contact times of 30 minutes or less and often an excellent yield can be obtained as soon as the exothermic reaction has begun which may be a matter of seconds. Speier et al. also teach that the reaction can be carried out at atmospheric, subatmospheric or superatmospheric pressures. The choice of conditions is a matter of logic based upon the nature of the reactants and the equipment available where nonvolatile reactants are adaptable to being heated at atmospheric pressure with or without reflux and gaseous reactants at ordinary temperatures are preferably reacted at substantially constant volume under autogenous or induced pressure wherein the best results are obtained by maintaining at least a portion of the reactants in the liquid phase.

Speier et al., as well as others, have been concerned with obtaining addition products from the reaction of aliphatically unsaturated compounds and silicon compounds having silicon-bonded-hydrogen atoms. However, none have suggested that there are situations where the product of such a reaction is an inhibitor for the very reaction by which it is made. Thus, the reaction begins but as soon as a small amount of product is produced the reaction stops because the products inhibit the reaction by poisoning the catalyst. The present invention is directed to a preparation of a unique class of compounds which inhibit the catalyst at low temperatures but not at high temperatures. Because the catalyst which is inhibited is used to make the inhibiting compound, the preparation method to provide a commercially suitable process was not obvious. The inhibiting compounds are a class of siloxane compounds containing olefinic unsaturation and are prepared from acetylenic alcohols and siloxane compounds having silicon-bonded-hydrogen atoms. The earliest work did not produce an inhibiting compound for the platinum catalyzed addition of aliphatic unsaturation to silicon-bonded hydrogen, but instead provided a complex mixture which may be called "a crosslinker-catalyst-inhibitor". This work is the subject of a copending application Ser. No. 528,962, filed Dec. 2, 1974, entitled "Crosslinker-Platinum Catalyst-Inhibitor and Method of Preparation Thereof" by Randolph G. Niemi and assigned to the same party. Niemi combined polysiloxane having multiple silicon-bonded hydrogen atoms, a platinum catalyst and an acetylenic alcohol, heated the mixture for about 16 hours at 70°C. and obtained a complex mixture after removing unreacted acetylenic alcohol by reduced pressure at room temperature, which when mixed with vinyl containing siloxane polymers remained uncured at room temperature but would cure at elevated temperatures. Thus, Niemi had found one could make room temperature stable compositions from his mixture, but for each composition a separate mixture of crosslinker, catalyst and acetylenic alcohol was required. Attempts to separate the complex mixture into various components were impractical and expensive. The product could not be characterized to identify any particular species which were responsible for the inhibiting effects on platinum catalysts.

Using the method of Niemi, Chi-Long Lee and Ollie W. Marko as described in a copending application Ser. No. 528,966, filed Dec. 2, 1974 entitled "Olefinic Siloxanes As Platinum Inhibitors" and assigned to the same party prepared specific olefinic siloxane compounds which were inhibitors for the platinum catalysts in the addition reaction between aliphatic unsaturation and silicon-bonded hydrogen atoms. For example, Lee and Marko mixed equal molar quantities of

(I)

and

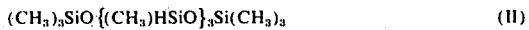

(II)

with a catalytic amount of a platinum catalyst from 2 to 50 parts per million platinum, heated the mixture at 70°C. for 16 hours, stripped off the unreacted starting ingredients, left set over night and then vacuum distillation was used to recover the product. The product was an olefinic siloxane compound of the formula

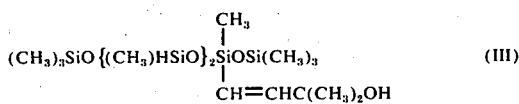 (III)

This compound mixed with a vinylsiloxane polymer, a silicon-bonded hydrogen containing compound and a platinum catalyst did not cure at room temperature in 10 days but when heated to 150°C. the composition cured in two minutes. Thus, this compound is a platinum catalyst inhibitor at room temperature, but not at elevated temperature.

Although Lee and Marko were able to characterize specific inhibitor compounds, the method of preparation was impractical. The process provided only a low conversion from 2 to 20 percent and the yield was less than 5 percent after distillation. In addition to both low conversion and yield, the reaction was difficult to control and could become violently exothermic, thus creating a safety hazard.

SUMMARY OF THE INVENTION

An object of this invention is to provide a method for preparing an olefinic siloxane compound which is an inhibitor for platinum at room temperature and which is not an inhibitor at elevated temperature.

This invention relates to a method for preparing olefinic siloxane compounds by coating the inside of an injection port of a GLC column with a layer of platinum catalyst, injecting a mixture of acetylenic alcohol and siloxane compound having at least three silicon-bonded hydrogen atoms where the injection port and column are heated. The product collected is an olefinic siloxane compound which contains silicon-bonded hydrogen atoms and which inhibits the reaction between aliphatically unsaturated compounds and silicon-bonded hydrogen atoms catalyzed by a platinum catalyst at room temperature but allows the reaction to occur at elevated temperatures.

DESCRIPTION OF THE INVENTION

This invention relates to a method of reacting an acetylenic alcohol with a siloxane compound having at least three silicon-bonded hydrogen atoms bonded to at least three different silicon atoms in the presence of a platinum catalyst to provide an olefinic siloxane compound wherein the olefinic siloxane compound is an inhibitor for the platinum catalyst comprising coating the inside of an injection port of a gas liquid chromatographic column with a layer of a platinum catalyst, heating the injection port to a temperature of from 300°C. to 375°C. and the column at a temperature from 100°C. to 375°C., injecting into the heated injection port and column a mixture of the acetylenic alcohol and the siloxane compound having at least three silicon-bonded hydrogen atoms with an inert carrier gas where residence times in said injection port are from 0.5 to 10 seconds and collecting from said column an olefinic siloxane compound which is, below 100°C., an inhibitor for the reaction between the acetylenic alcohol and the siloxane compound having at least three silicon-bonded-hydrogen atoms in the presence of a platinum catalyst.

The method of this invention can be operated as a continuous method fully automated or it can be operated in a one shot manner by manual injections with a syringe and variations therebetween, depending upon the degree of sophistication one wishes to use. The basic equipment necessary to operate this invention are those of conventional gas liquid chromatographic (hereinafter referred to as GLC) units, namely an injection port capable of being heated, a column with a unit for heating, a detection unit or analyzer, a collection point which may be cooled and a means for inputting inert carrier gas. The nature and style of the GLC unit used is unimportant except for those specific characteristics discussed herein.

The injection port should be of stainless steel or other substances which do not interfere with the present method, such as quartz or glass. The injection port is coated on the inside with a layer of a platinum catalyst. The coating can be done in any manner such as by injecting the platinum catalyst dissolved in a solvent into the injection port wherein the catalyst is deposited from the solution onto the injection port surface. The only requirement for the platinum catalyst is that it be in a form so that it can be coated on the surface of the injection port, especially from a solution. It is within the scope of this invention to use metallic platinum which has been coated on the inside surface of the injection port. However, because this type of coating would be expensive and wasteful of platinum, the soluble platinum catalysts are preferred. By soluble platinum catalyst it is to be understood that any platinum catalyst which can be put into a solution wherein the solvent can be removed and the platinum catalyst deposited without damaging the injection port or other GLC equipment is within the scope of soluble platinum catalyst. Because the solvent for the platinum catalyst does not remain in the system, there is no need to be concerned about its potential reactivity with the reactants of the method of this invention.

The GLC column can be packed with a variety of materials known for packing such columns, however, one should predetermine if a particular packing is suitable for the temperature ranges to be used and whether the reactants or products are reactive with the material to be used. For example, the column can be packed with supports of commercially available screened calcined diatomic aggregates which have been acid washed and treated with dimethyldichlorosilane. The packing is coated with a non-volatile polyethyleneglycol or a polydiorganosiloxane. The polyethyleneglycol can be used up to temperatures of about 200°C. and the polydiorganosiloxanes can be used up to temperatures of 375°C. or higher. The column can vary in diameter and length depending on ones needs.

The injection port is heated to a temperature from 300°C. to 375°C. Below a temperature of 300°C., the reaction is too slow to be practical and no useful quantities of adduct product is obtained. Above 375°C., the amount of degradation is sufficiently high and becomes the dominating product with little or no useful adduct product obtained. Preferably, the injection port is heated from 325°C. to 360°C., where optimum yields of useful product are obtained.

The column, usually enclosed in an oven, is heated to a temperature between 100°C. and 375°C. Below a temperature of 100°C., no useful amounts of adduct product is obtained and above 375°C. degradation of the product occurs and no useful amount of adduct product is obtained. Preferably, the column is heated from 200°C. to 360°C. for optimum results. The column can be heated at one temperature, isothermal, or it can be programmed to operate at a defined rate of increase over a temperature range such as from 100°C. to 350°C. at 20°C. per minute. Preferably, the column is heated at a single temperature because the operation can be made continuous more conveniently.

After the injection port and column have been heated to the operating temperatures, a mixture of the acetylenic alcohol and the siloxane compound having at least three silicon-bonded hydrogen atoms per molecule is injected into the injection port. The residence time in the injection port can be varied from 0.5 to 10 seconds, preferably 1 or 2 seconds. The injection can be done at one time, where the amounts are usually small or small amounts can be injected at various time intervals. For sufficient quantities of product, it is preferred to inject small amounts at intervals such as every 10 to 60 seconds. The injection of reactants can be done automatically for convenience. The mixture injected into the injection port is transported in vapor form by an inert carrier gas through the column. The inert carrier gases can be any of those gases conventionally used in GLC units, such as helium, neon, argon or nitrogen. Reactive gases should not be used, such as hydrogen gas.

The product is collected as it comes through the column. The material coming out of the column will be unreacted starting species, as well as, adduct product and thus the GLC unit should preferably contain a detector or analyzer which can be used to determine unreacted starting materials from adduct product so as to not collect them together. By separating the materials as they are collected, the products are collected in high purity and need not be further distilled. One of the main features of this method is that the olefinic siloxane compounds can be obtained in high purity and thus the collection of the olefinic siloxane compound separated from the unreacted starting material is a real advantage.

The present method also permits the use of a wide range of reactants and is particularly useful for products which cannot be readily distilled because of degradation problems or because they have boiling points close to the reactants. Thus, although this method is not broadly applicable to commercialization because of problems encountered with the plugging of the column, it is useful to prepare certain compounds which are not readily prepared by other methods. Under long usage the column may plug and requires cleaning before continuing to produce more product. For this reason, the manufacture of large quantities is not practical. However, for small quantities of all materials and for specific products not readily obtained by other means in high purity, this method offers a unique means of obtaining these products. This method also provides the products, free of platinum or platinum catalysts which are sometimes difficult to eliminate by other methods.

The yield of product can be increased by adding 1 to 15 parts by weight platinum per one million parts by weight of mixture in the form of a platinum catalyst to the mixture of acetylenic alcohol and the siloxane compound having at least three silicon-bonded hydrogen atoms per molecule. The use of platinum catalyst in this manner, however, can hasten the time plugging of the column takes place. Also observed was that an increase in size of the GLC column resulted in a decrease in yield. The particular yield which one finds acceptable will depend upon the desirability of the product and the ability to recycle starting materials.

The acetylenic alcohol can be any of those alcohols having a C $\equiv$ C bond which when reacted with a siloxane compound having SiH results in an olefinic containing siloxane which are inhibitors for platinum catalyst at room temperature but not at elevated temperatures above 100°C. Examples of such acetylenic alcohols, include, 3-methyl-1-butyn-3-ol, 1-ethynylcyclohexan-1-ol, 3,5-dimethyl-1-hexyn-3-ol, 3-methyl-1pentyn-3-ol and the like.

The siloxane compounds are those having at least three silicon-bonded hydrogen atoms bonded to at least three separate silicon atoms. These siloxane compounds can be straight chains, cyclics, or branched. These siloxanes can be copolymers, homopolymers, single species, mixtures of the various types mentioned above. It is preferred that these siloxane compounds have at least two silicon-bonded hydrogen atoms bonded to silicon atoms separated by one oxygen atom, preferably three silicon-bonded hydrogen atoms bonded to three silicon atoms which are only separated by oxygen. Some of the siloxane compounds for use in the present method are defined by the following generic formulae,

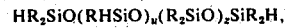
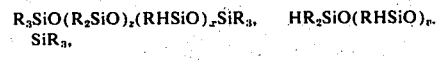
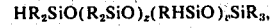
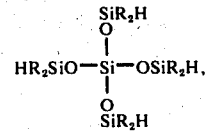

and the like, wherein each R is a monovalent hydrocarbon radical having no aliphatic unsaturation such as methyl, ethyl, phenyl, propyl, hexyl, cyclohexyl, octyl, dodecyl, cyclopentyl, isopropyl, or fluorinated monovalent hydrocarbon radicals such as 3,3,3-trifluoropropyl, other perfluoroalkylethyl radicals, α,α, α-trifluoromethylphenyl, hexafluorophenyl and the like. The number of siloxane units per molecule can vary from as little as 3 to any number which can be passed through the system, preferably from 3 to 10 siloxane units per molecule. Other siloxane compounds are also suitable such as those which have arylene or alkylene bonds between some of the silicon atoms. Some specific siloxane compounds include

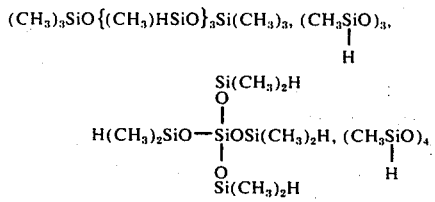

and the like.

The platinum catalyst is not narrowly critical and can be chloroplatinic acid, platinum chlorides, platinum salts, platinum metal coated on the injection port, platinous halide complexes with olefins and other well known platinum catalysts. These and other platinum catalysts are further defined and illustrated in U.S. Pat. No. 3,453,234, issued July 1, 1969 to Gust J. Kookootsedes, and hereby included by reference to illustrate platinum catalyst.

The amount of acetylenic alcohol and siloxane compound having silicon-bonded hydrogen atoms can vary broadly. Molar ratios of one to one have been found to be the most suitable. Other ratios would result in lower yields and are thus not considered to be the most practical.

The method of this invention produces an olefinic siloxane compound which is the addition product of the acetylenic alcohol and the siloxane compound having at least three silicon-bonded hydrogen atoms. The addition products, which are produced in major amounts and which are the inhibitors, are those which do not add to all the silicon-bonded hydrogen atoms. There should be at least one unreacted silicon-bonded hydrogen bond per molecule of olefinic siloxane compound. The method of this invention provides addition products, which are inhibitors, in yields of up to 35 weight percent mono-adduct. Both the mono- and di-adducts are inhibitors, however, when all the silicon-bonded hydrogen atoms are reacted the product is markedly reduced in inhibition activity.

The olefinic siloxane compound inhibitors are useful in that these compounds retard the room temperature reaction of vinyl compounds with silicon-bonded hydrogen atoms which are catalyzed with platinum but allow the reaction to occur rapidly at elevated temperature such as at 150°C. Thus, these olefinic siloxane compounds can be used to make one package compositions which cure on heating but are stable over extended periods of time at ambient conditions.

The following examples are presented for illustrative purposes and should not be construed as limiting the invention which is properly delineated in the appended claims.

EXAMPLE 1

The stainless steel injection port of a GLC unit was coated with platinum catalyst by injecting a solution of chloroplatinic acid hexahydrate in isopropanol. The alcohol was then removed and the injection port was heated to 350°C., a 4-foot packed column (1.219 meter column) was heated to 240°C. and an equal molar mixture of 3-methyl-1-butyn-3-ol and the siloxane of formula (II) was injected through the coated injection port. A detector at 350°C. was used and the mono-adduct represented by formula (III) was collected in a yield of about 30 weight percent. The mono-adduct had a boiling point of 265°C. The column was packed with a commercially available screened calcined diatomic aggregate which was acid washed and treated with dimethyldichlorosilane as the support for a non-volatile polydimethylsiloxane containing about 5 mole percent phenyl radicals where the polydimethylsiloxane was about 10 weight percent of the packing.

The above procedure was repeated except that one part by weight platinum in the form of chloroplatinic acid hexahydrate per million parts by weight mixture was combined with the mixture. The same product was collected but in a yield of about 35 weight percent.

Repeating the above procedure wherein one p.p.m. of platinum was used but the injection port temperature was 310°C. and the column temperature was 250°C., resulted in collecting a much smaller yield of the mono-adduct.

EXAMPLE 2

The above procedure was followed except the column temperature was programmed to increase at a rate of 30°C. per minute from 100°C. to 300°C. and the mixture as defined in the Table contained 10 parts by weight platinum per one million parts by weight mixture and was in the form of a platinum catalyst complex of chloroplatinic acid hexahydrate and symmetrical divinyltetramethyldisiloxane. The products collected were mono-adducts as defined in the Table and had the boiling points indicated by the peak temperature as it came off the column.

Table

| Acetylenic Alcohol | Siloxane | Mono-adduct | Elution Temperature, °C. |
|---|---|---|---|
| $HC{\equiv}C{-}\underset{\underset{CH_3}{\mid}}{\overset{\overset{CH_3}{\mid}}{C}}OH$ | ${\{(CH_3)HSiO\}}_4$ | $\begin{array}{c}\overset{CH_3}{\underset{\mid}{HSi}}{-}O{-}\overset{CH_3}{\underset{\mid}{SiH}}\\ \underset{\mid}{O}\quad\underset{\mid}{O}\\ \overset{}{\underset{\underset{CH_3}{\mid}}{HSi}}{-}O{-}\overset{}{\underset{\underset{CH_3}{\mid}}{Si}}{-}CH{=}CH\overset{CH_3}{\underset{\underset{CH_3}{\mid}}{C}}OH\end{array}$ | 200 |

Table-continued

| Acetylenic Alcohol | Siloxane | Mono-adduct | Elution Temperature, °C |
|---|---|---|---|
| $HC\equiv C-\underset{\underset{C_6H_5}{\mid}}{\overset{\overset{CH_3}{\mid}}{C}}-OH$ | $[(CH_3)HSiO]_4$ | (cyclic tetrasiloxane with three SiH groups and one Si–CH=CH–C(CH₃)(C₆H₅)OH group) | 263 |
| $HC\equiv C-\underset{\underset{C_6H_5}{\mid}}{\overset{\overset{CH_3}{\mid}}{C}}-OH$ | $(CH_3)_3SiO\underset{\underset{H}{\mid}}{\overset{\overset{CH_3}{\mid}}{Si}}-O-\underset{\underset{H}{\mid}}{\overset{\overset{CH_3}{\mid}}{Si}}-O-\underset{\underset{H}{\mid}}{\overset{\overset{CH_3}{\mid}}{Si}}OSi(CH_3)_3$ | $(CH_3)_3SiO\underset{\underset{H}{\mid}}{\overset{\overset{CH_3}{\mid}}{Si}}-O-\underset{\underset{\underset{\underset{C_6H_5}{\mid}}{CHCOH}}{\overset{\overset{CH_3}{\mid}}{\|}}}{\overset{\overset{CH_3}{\mid}}{Si}}-O-\underset{\underset{H}{\mid}}{\overset{\overset{CH_3}{\mid}}{Si}}OSi(CH_3)_3$ | 293 |

EXAMPLE 3

A composition was prepared by thoroughly mixing 63 grams of a phenylmethylvinylsiloxy endblocked polydimethylsiloxane having a viscosity of 400 centistokes at 25°C., 33 grams of five micron quartz and 12 parts by weight platinum per one million parts by weight total composition wherein the platinum was added in the form of the platinum catalyst complex defined in Example 2. To this mixture was added and thoroughly mixed in 4.86 grams of trimethylsiloxy endblocked polyorganosiloxane having an average of five methylhydrogensiloxane units and three dimethylsiloxane units. The resulting mixture cured at room temperature to a coherent solid elastomer in one hour and at 150°C. cured to an elastomer in two minutes. The above composition was prepared again except 0.00166 moles of the mono-adduct of formula (III) was mixed with the hydrogen containing trimethylsiloxy endblocked polyorganosiloxane. This mixture cured at 150°C. to an elastomer in two minutes, but did not cure at room temperature in 10 days.

That which is claimed is:

1. A method of reacting an acetylenic alcohol with a siloxane compound having at least three silicon-bonded hydrogen atoms bonded to at least three different silicon atoms in the presence of a platinum catalyst to provide an olefinic siloxane compound wherein the olefinic siloxane compound is an inhibitor for the platinum catalyst comprising coating the inside of an injection port of a gas liquid chromatographic column with a layer of a platinum catalyst, heating the injection port to a temperature of from 300°C. to 375°C. and the column at a temperature from 100°C. to 375°C., injecting into the heated injection port and column a mixture of the acetylenic alcohol and the siloxane compound having at least three silicon-bonded-hydrogen atoms with an inert carrier gas where residence times in said injection port are from 0.5 to 10 seconds and collecting from said column an olefinic siloxane compound which is, below 100°C., an inhibitor for the reaction betwen the acetylenic alcohol and the siloxane compound having at least three silicon-bonded-hydrogen atoms in the presence of a platinum catalyst.

2. The method in accordance with claim 1 in which there is present in said mixture from 1 to 15 parts by weight platinum per one million parts by weight mixture where the platinum is in the form of a platinum catalyst.

3. The method in accordance with claim 1 in which the injection port temperature is from 325°C. to 360°C. and the column temperature is from 200°C. to 360°C.

4. The method in accordance with claim 1 in which the acetylenic alcohol is 3-methyl-1-butyn-3-ol.

5. The method in accordance with claim 2 in which the acetylenic alcohol is 3-methyl-1-butyn-3-ol.

6. The method in accordance with claim 3 in which the acetylenic alcohol is 3-methyl-1-butyn-3-ol.

7. The method in accordance with claim 4 in which the siloxane compound having at least three silicon-bonded hydrogen atoms in an organosiloxane having two trimethylsiloxy units and three methylhydrogensiloxane units.

8. The method in accordance with claim 5 in which the siloxane compound having at least three silicon-bonded hydrogen atoms is an organosiloxane having two trimethylsiloxy units and three methylhydrogensiloxane units.

9. The method in accordance with claim 6 in which the siloxane compound having at least three silicon-bonded hydrogen atoms is an organosiloxane having two trimethylsiloxy units and three methylhydrogensiloxane units.

\* \* \* \* \*